United States Patent
Uchida et al.

[11] Patent Number: 5,980,866
[45] Date of Patent: Nov. 9, 1999

[54] TISSUE ADHESIVE SUITABLE FOR SPRAY APPLICATION

[75] Inventors: Takanori Uchida, Kumamoto; Hiroshi Kaetsu, Nishigoushi-machi; Nobuto Fukunaga, Tamana; Noriko Shinya, Kumamoto; Takahiro Sakamoto, Goushi-machi, all of Japan

[73] Assignee: Juridical Foundation The Chemosero-Therapeutic Research Institute, Kumamoto, Japan

[21] Appl. No.: 08/945,882

[22] PCT Filed: Mar. 14, 1997

[86] PCT No.: PCT/JP97/00818

§ 371 Date: Nov. 13, 1997

§ 102(e) Date: Nov. 13, 1997

[87] PCT Pub. No.: WO97/33633

PCT Pub. Date: Sep. 18, 1997

[30] Foreign Application Priority Data

Mar. 15, 1996 [JP] Japan .................................. 8-087566

[51] Int. Cl.$^6$ .............................. A61L 9/14; A61L 25/00; A61L 15/58
[52] U.S. Cl. .......................... 424/45; 530/380; 530/381; 530/382; 530/303; 530/384; 514/822
[58] Field of Search .............................. 424/45; 530/380, 530/381, 382, 383, 384; 514/822

[56] References Cited

U.S. PATENT DOCUMENTS 4,427,651 1/1984 Stroetmann ................................ 424/46
4,983,386 1/1991 Kamishita et al. ....................... 424/78
5,030,215 7/1991 Morse et al. ............................. 604/410
5,461,081 10/1995 Ali et al. ................................. 514/772.3
5,582,596 12/1996 Fukunaga et al. ....................... 604/191

FOREIGN PATENT DOCUMENTS 61-293443 12/1986 Japan .
WO 94/07420 4/1994 WIPO .

OTHER PUBLICATIONS

Kiso to Rinsho (Basic and Clinical Report), vol. 20, No. 4, pp. 2399–2405, Mar. 1986.

Hiroshi Kaetsu, et al., The Clinical Report, vol. 23, No. 10, pp. 3735–3743, "Studies on the Optimal Compounding Ratio of Fibrin Adhesive", Jul. 1989.

*Primary Examiner*—Thurman K. Page
*Assistant Examiner*—Lakshmi Channavajjala
*Attorney, Agent, or Firm*—Oblon, Spivak, McClelland, Maier & Neustadt, P.C.

[57] ABSTRACT

An adhesive for tissue capable of uniformly forming a high concentration of fibrin so as to provide a high closing effect is disclosed. The adhesive for tissue comprises a fibrinogen solution and a thrombin solution which solutions are separated from each other. The adhesive is to be mixed and spray coated together with a sterile gas and has a volume ratio of the fibrinogen solution to the thrombin solution of about 2:1 to 10:1. This adhesive is to be sprayed together with a sterile gas for the adhesion or closing of living tissue of a human being or animal.

10 Claims, 3 Drawing Sheets

TISSUE ADHESIVE SUITABLE FOR SPRAY APPLICATION

This application is a 371 of PCT/JP97/00818, filed Mar. 14, 1997.

TECHNICAL FIELD OF THE INVENTION

The present invention relates to an adhesive for tissue, which is to be used in the form of a two-pack type preparation and which is suitable for the uniform application of the adhesive at a concentration higher than that of an ordinary adhesive. In particular, the present invention relates to an adhesive for tissue (hereinafter referred to as tissue adhesive) suitable for the use in a method wherein a protein solution containing fibrinogen as the essential component and a thrombin solution are sprayed and also suitable for lowering the volume ratio of a thrombin solution to a fibrinogen solution of a high concentration so as to uniformly form fibrin of a high-concentration, whereby obtaining a high closing effect.

BACKGROUND OF THE INVENTION

Fibrinogen is a clotting factor having a very important role in the final stage of the so-called blood-coagulation cascade. In the activation of, for example, the blood clotting system after a damage, soluble fibrinogen is converted, by thrombin, into insoluble fibrin which has an important role of contributing to the hemostasis and curing of a wound. Recently, a tissue adhesive was developed taking advantage of this theory in the final phase of the blood clotting, and it is now used as an adhesive in place of a suture of a soft organ such as liver or spleen or as a suture assistant in a surgical operation. A tissue adhesive is widely used also in other clinical situation.

For the application of the tissue adhesive to an affected part of the body, a "sequential method" wherein a fibrinogen solution and a thrombin solution are applied alternately to form a laminate coat or a "simultaneous method" wherein both the fibrinogen solution and thrombin solution are applied simultaneously to mix them together was mainly employed. However, the sequential method has a problem in that a major part of the fibrinogen solution flows down prior to the formation of a fibrin gel, and also the simultaneous method has a problem in that the formed fibrin gel is heterogeneous. Therefore, the effect of the tissue adhesive was limited in both the sequential method and simutaneous method.

Recently, a spray method has just started to be spread for solving the above-described problems. In this method, a fibrinogen solution and a thrombin solution in each syringe are simultaneously ejected together with a sterile gas to spray these two solutions in the form of a mist mixture. A preferred example of the devices for this method is described in International Patent Publication (PCT WO94-07420). However, even such a spray method has a problem to be solved for obtaining a complete effect of the tissue adhesive when a strong adhesion and closing effect are demanded in, for example, the treatment of great vessels and also the treatment of air leak in the lungs.

Investigations were made for improving the effect of the tissue adhesive by increasing the concentration of fibrinogen to find that, although the clotting strength and adhesive power of the fibrin gel obtained by the sequantial method are increased as the final concentration of fibrinogen in the mixture of the two components is increased, they are no more increased even when the final concentration of fibrinogen is increased to about 4% or higher [see "Kiso to Rinsho" (Basic and Clinical Report), 20, 2399 to 2405 (1986), and 23, 3735 to 3743 (1989)]. However, when the sequential method is employed, the fibrin gel obtained by such a test cannot be uniformly applied. Thus, it cannot be said that the advantage of the increase in the final concentration of fibrinogen has been put to practical use.

Japanese Patent Unexamined Published Application (hereinafter referred to as "J. P. KOKAI") No. Sho 61-293443 discloses a method for increasing the final concentration of fibrinogen in the mixture of the two components by changing the mixing ratio of the fibrinogen solution to the thrombin solution in its specification (in particular, in the "test results" in the detailed description of the Invention). In this specification, it is described that the limiting tensile strength depends on the final concentration of fibrinogen after mixing the two components.

However, in these tests, the adhesive is applied by so-called "mixing method" and, in addition, the final concentration of thrombin in the formation of the fibrin gel after mixing the two components is as low as 1 to 2 units/ml. Such a low thrombin concentration is far apart from the thrombin concentration (250 to 500 units/ml) actually employed in the clinical sites. It is known that particularly when the thrombin concentration is low, the clotting of fibrinogen necessitates a long period of time and, in addition, a sufficient hemostasis effect cannot be obtained in the closing treatment of the tissue. Although a test wherein the final concentration of thrombin after mixing the two components is as high as 500 units/ml is described therein, it is stated therein that the limiting tensile strength could not be determined. This fact suggests that the tests given in J. P. KOKAI No. Sho 61-293443 are unsuitable for the determination of the effects of the tissue adhesive to be used in a clinical site.

The main object of the invention disclosed in J. P. KOKAI No. Sho 61-293443 is to provide a device for preparing a fibrinogen solution from a freeze-dried preparation previously charged in a syringe, which is capable of shortening the dissolution time without reducing the limiting tensile strength of the adhesive. In this invention, the mixing ratio is varied so that a limiting tensile strength equal to that of an ordinary product (a concentration is 10% before the mixing) can be obtained even when the concentration of the fibrinogen solution is lowered. Therefore, the concentration described therein is not the practical one, and this invention does not provide any means for adhering a tissue which is suitable for the actual use for particularly obtaining a high effect of closing the wound.

Therefore, the object of the present invention is to provide a tissue adhesive suitable for spray application, which is to be used in the form of a two-pack preparation and which can be used at a high concentration and uniformly sprayed.

Another object of the present invention is to provide a tissue adhesive capable of uniformly forming fibrin of a high concentration to provide a high closing effect.

After intensive investigations made for the purpose of attaining the above-described objects, and on the basis of an idea that the spray method wherein the fibrinogen solution and thrombin solution can be homogeneously mixed together is the best method for the application of the tissue adhesive, the inventors have found the following fact: for improving the effect of fibrinogen by increasing the final concentration of fibrinogen in the mixture of the two components, it is effective that the concentration of fibrinogen which can be sprayed is made as high as possible and also that the mixing ratio of the fibrinogen solution and thrombin solution is changed. Further, the structure of a device for conducting this method has been made clear, and the present invention capable of providing the tissue adhesive suitable for use in a method wherein a remarkable effect is obtained has been completed.

DISCLOSURE OF THE INVENTION

The present invention relates to a tissue adhesive comprising a fibrinogen solution and a thrombin solution which solutions are separate from each other and to be mixed and sprayed together by means of a sterile gas for adhering or closing a wound of a living tissue of a human being or an animal, wherein the volume ratio of the fibrinogen solution to the thrombin solution is about 2:1 to 10:1.

PREFERRED EMBODIMENTS FOR PRACTICING THE INVENTION

The object of the present invention is to obtain a high closing effect by changing the mixing volume ratio of the fibrinogen solution to the thrombin solution of 1:1 which was conventionally used in the prior art so as to reduce the volume ratio of the thrombin solution to the fibrinogen solution, so that when both the solutions are sprayed, fibrin of a high concentration is uniformly formed. From this viewpoint, the suitable concentrations of the fibrinogen solution and the thrombin solution are 4 to 15% (w/v, 40 to 150 mg/ml), preferably 7 to 12% (w/v, 70 to 120 mg/ml), and 100 to 10,000 units/ml (Japanese Phamacopoeia or NIH units based on the US Standard Thrombin), preferably 250 to 5,000 units/ml (NHI units), respectively. The mixing ratio of them is preferably about 2:1 to 10:1 (volume ratio), particularly 2:1 to 5:1.

Figure 3:
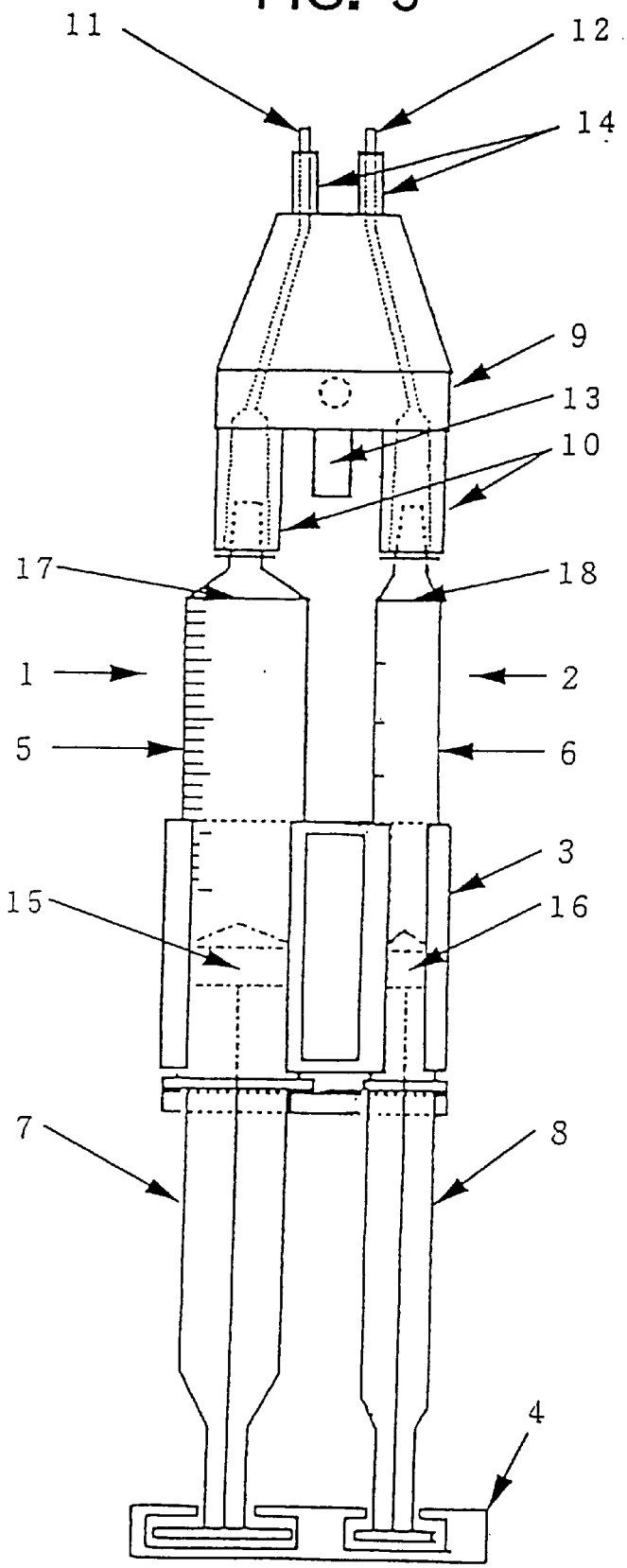
FIG. 3 is a plan view of a device suitable for spraying the tissue adhesive of the present invention.

Although it is difficult to mix the two components in a precise mixing ratio other than 1:1 by using the two separate syringes, such a mixing can be conducted preferably by using an application device suitable for the tissue adhesive of the present invention, which is shown in FIG. 3.

In this device, a syringe containing the fibrinogen solution has an effective stroke having a length equal to that of another syringe containing the thrombin solution, and the cross section of the syringe containing the fibrinogen solution is about 2 to 10 times as large as that of the syringe containing the thrombin solution. By operating the pistons of both syringes integrally, both solutions in a volume ratio determined according to the cross sections of the two syringes are extruded through a pipe to a sterile gas jet opening in a spray head to form a mist. The adhesive is thus spray coated.

The present invention provides a more desirable mode of the tissue adhesive suitable for the spray coating. When a fibrinogen solution is to be sprayed with a spraying device, it was difficult to spray the fibrinogen solution having a concentration of as high as above 10% (100 mg/ml) in the prior art. However, the viscosity of the fibrinogen solution can be remarkably lowered by adding a viscosity-lowering agent to the solution so that the solution can be sprayed in a suitable manner. Particularly when a high adhesion strength is necessitated, the uniform spraying is made possible by lowering the viscosity even when the fibrinogen content is about 10% (100 mg/ml) or higher. The object of the invention can be thus attained.

By increasing the concentration of the fibrinogen solution to be mixed with the thrombin solution, the final concentration of fibrinogen which was increased by changing the mixing ratio is further increased and the effect thereof is further improved. The viscosity-lowering agents which are not particularly limited herein include, for example, guanidino group-containing substances such as arginine and guanidine. Arginine or the like is particularly preferably used. The viscosity-reducing agents are usable either alone or in combination of two or more of them. The amount of the viscosity-reducing agent is preferably 0.1 to 1.0 M, particularly preferably 0.1 to 0.5 M.

According to the present invention, the tissue adhesive having a high closing effect can be obtained by uniformly forming fibrin of a high concentration.

The following Test Examples and Working Examples will further illustrate the present invention, which by no means limit the scope of the present invention.

EXAMPLES

Test Example 1

The test was conducted by using "Bolheal" [a product of the Chemo-Sero-therapeutic Research Institute] which is a commercial two-component adhesive for living tissue. This preparation had a fibrinogen concentration of 8% and thrombin concentration of 250 units/ml.

Figure 1:
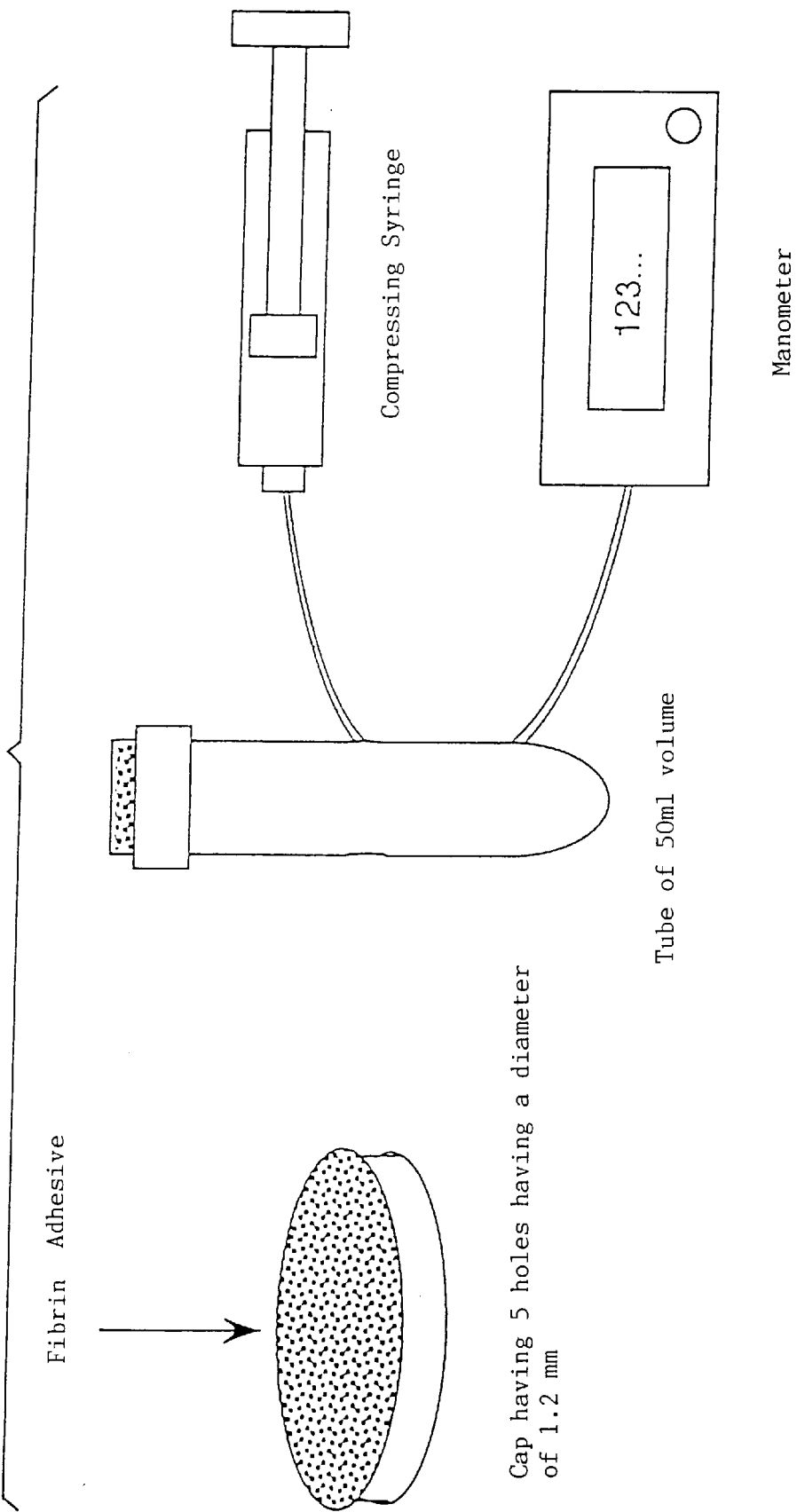
FIG. 1 is a drawing showing the method for determining the closing effect.

The closing effect was evaluated by means of a device shown in FIG. 1. In the test, five holes having a diameter of 1.2 mm were bored in a cap of a plastic test tube which was then connected with a manometer and a compressing syringe. A tissue adhesive comprising the two solutions in a varied mixing ratio was applied to the cap by the spray method or sequential method. Ten minutes after the formation of the adhesive, air in the tube was compressed with the syringe and the pressure (burst pressure: mmHg) at the moment of starting the air leak through the fibrin gel was recorded. The mixing ratio of the fibrinogen solution to the thrombin solution was 1:1 or 5:1. The amount of the fibrinogen solution used was 0.85 ml in all the cases.

Figure 2:
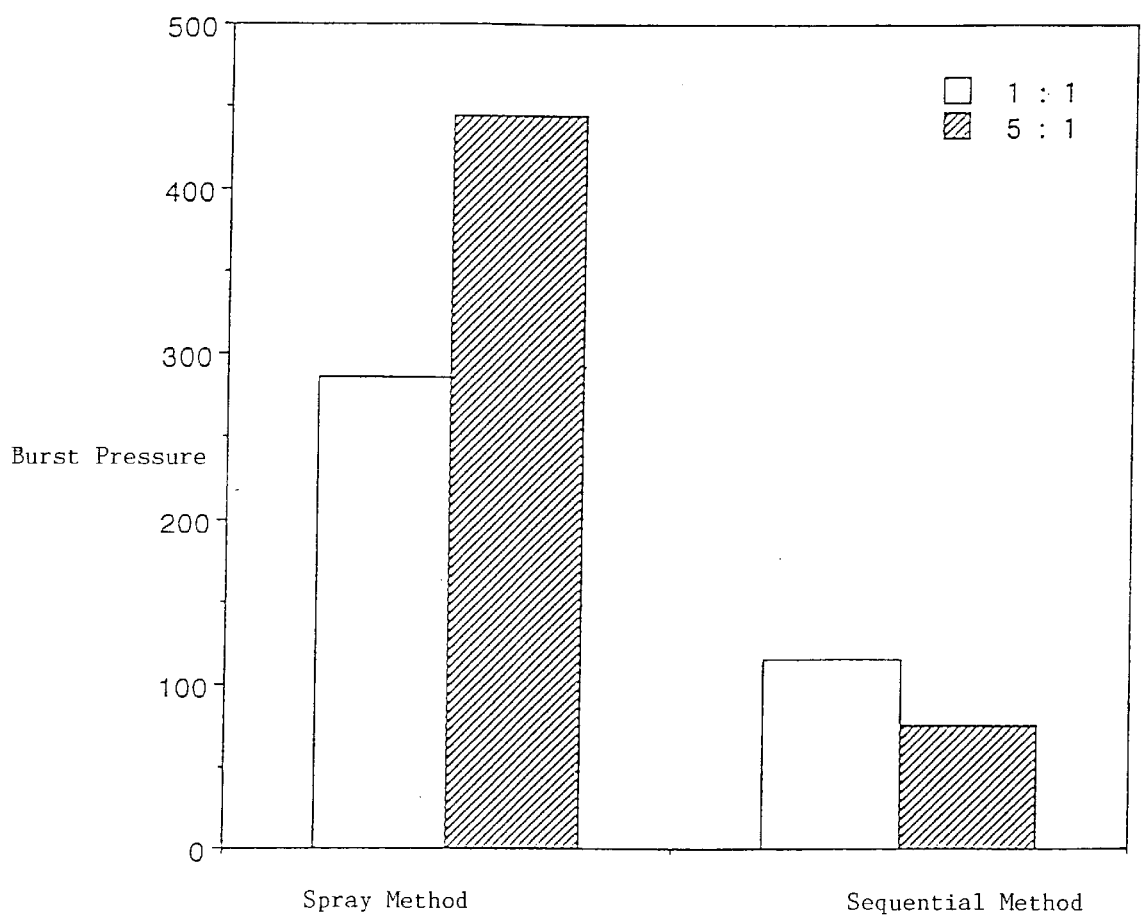
FIG. 2 is a graph showing the change in closing effect by changing the mixing ratio in both spray method and sequential method.

As shown in FIG. 2, when the mixing ratio was changed from 1:1 to 5:1, the burst pressure was remarkably elevated from 287 mmHg to 445 mmHg in the spray method, while it was lowered in the sequential method. The burst pressure of 445 mmHg obtained by changing the mixing ratio in the spray coating was an extremely high pressure which could not be obtained in the prior art.

Test Example 2

The test was conducted by using "Bolheal" [a product of the Chemo-Sero-therapeutic Research Institute] which is a commercial two-component adhesive for living tissues. This preparation had a fibrinogen concentration of 8% and thrombin concentration of 250 units/ml.

The closing effect was evaluated on the basis of the air leak-preventing capacity in the lungs of rats. In the test, a tracheal tube was inserted into the trachea of a rat and fixed therein at one end thereof by the ligation. The other end of the tracheal tube was connected with a cannula, trigonal stopcock, manometer and compressing syringe. After confirming no air leak, the pressure was controlled with the syringe so that the manometer indicated 15 mmHg. A hole having a diameter of 1.2 mm was bored in the lung with a needle, and a tissue adhesive having a given mixing ratio was spray coated on the air leak portion. 10 minutes after the formation of the adhesive, saline was applied to the lung, the pressure was elevated with the syringe, and the pressure (burst pressure: mmHg) under which the air leak of the lung began was recorded. The mixing ratio of the fibrinogen solution to the thrombin solution was 1:1 or 5:1. The amount of the fibrinogen solution used was 0.15 ml in all the cases.

As shown in the following Table 1, the burst pressure was remarkably elevated from 27.8 mmHg to 49.4 mmHg by changing the mixing ratio from 1:1 to 5:1.

TABLE 1

| Burst pressure | Order of times of determination | | | | | | | | |
|---|---|---|---|---|---|---|---|---|---|
| (mmHg) | 1 | 2 | 3 | 4 | 5 | 6 | 7 | 8 | Average ± S.D. |
| Mixing ratio | | | | | | | | | |
| 1:1 | 16 | 25 | 31 | 32 | 43 | 32 | 20 | 23 | 27.8 ± 8.5 |
| 5:1 | 40 | 64 | 42 | 40 | 67 | 42 | 42 | 58 | 49.4 ± 11.6 |

Test Example 3

A solution having a coagulating protein concentration of 7.5 toll. 1% (w/v) was prepared from fibrinogen prepared by a combination of a cold ethanol precipitation method with a method wherein the solubility of fibrinogen is lowered by glycine or by a glycine precipitation method wherein glycine is used alone. The viscosity (mPa.s) of each solution was determined at 37° C. to find that a high viscosity resulted depending on the coagulating protein concentration. Particularly when the coagulating protein concentration was 11.1%, the viscosity was as high as 152.2 mPa.s. However, when arginine was added to the 11.1% solution so that the final arginine concentration would be 0.1 to 0.5 M, the viscosity became 77.4 to 84.2 mPa.s. This fact proved the viscosity-lowering effect of arginine. The results were as shown in the following Table 2.

TABLE 2

| Arginine conc. (M) | Coagulating protein conc. (%) | Viscosity of solution (mPa • s) |
|---|---|---|
| 0.0 | 7.5 | 18.2 |
| 0.0 | 7.9 | 24.2 |
| 0.0 | 8.8 | 36.2 |
| 0.0 | 9.7 | 61.5 |
| 0.0 | 11.1 | 152.2 |
| 0.1 | 11.1 | 82.8 |
| 0.2 | 11.1 | 84.2 |
| 0.3 | 11.1 | 77.4 |
| 0.4 | 11.1 | 77.4 |
| 0.5 | 11.1 | 78.5 |

Example 1

An example of the application of the tissue adhesive of the present invention by means of a suitable applicating device will be described below with reference to the drawing.

FIG. 3 is a plan view of a device suitable for spraying the tissue adhesive of the present invention. The device for spraying the tissue adhesive is composed of a syringe (1) containing the fibrinogen solution, a syringe (2) containing the thrombin solution, a syringe-holding means (3) for fixing each syringe at its barrel (5 or 6) part, an integrally operating means (4) placed at the end of a plunger (7 or 8) of each syringe for operating the plunger (7 or 8), integrally, and a spray head (9) at the syringe ends.

As shown in FIG. 3, the cross section of the syringe (1) is larger than that of the syringe (2). In an embodiment shown in FIG. 3, the cross section ratio is 5:1 and, therefore, the volume ratio is also 5:1. The effective stroke, i.e. the distances from the end faces at the exits (17 or 18) to the inserted pistons (15 or 16) of the two syringes (1 and 2) are equal.

A sterile gas is introduced into a spray head (9) through a sterile gas-feeding passage (13), and jetted through a sterile gas-jet opening (14). At the same time, an integrally operating means (4) for the syringe (1) containing the fibrinogen solution and the syringe (2) containing the thrombin solution is pressed to extrude both solutions, in a volume ratio which varies depending on the cross sections of the syringes, in the form of a mist through the passages in the spray head (9) and tubes (11 and 12). The adhesive is thus sprayed.

The syringes (1 and 2) are usually made from glass or a transparent synthetic resin such as a polypropylene or a polycarbonate. The syringes (1 and 2) are each composed of a barrel (5 or 6) having a narrowed part to be connected with the spray head (9) and a smoothly slidable plunger (7 or 8) inserted into the barrel (5 or 6).

The sterile gas passed through an air filter is fed into the spray head (9) through the sterile gas-feeding passage (13), and then jetted through the sterile gas-jet opening (14). In the spray head (9), the tubes (11 and 12) for feeding the fibrinogen solution and thrombin solution are arranged from syringe-connecting ports (10) toward the sterile gas-jet opening (14). Although the materials for the spray head (9) are not particularly limited, they are usually soft resins such as vinyl chloride resin, polyethylene, polyesters and polypropylene, and metals having a high processability. The tubes (11 and 12) are made of Teflon, vinyl chloride resin, a metal or the like.

The syringe-holding means (3) is to fix the syringes (1) and (2), integrally. The shapes of the syringe-holding means (3) can be various, and the shape shown in FIG. 3 is one of them. In one face of the syringe-holding means (3), two grooves having shapes corresponding to the shapes of the outer walls of the barrels (5 and 6) are formed in parallel. The depth of the grooves is larger than the radius of the cross section of the barrel (5 or 6). Therefore, the inlet of the groove is narrow so that when the barrel (5 or 6) is fixed into the groove, the barrel (5 or 6) will be kept by the grooved wall.

The integrally operating means (4) fixes the pressing parts of the two plungers (7 and 8) so as to integrally move these plungers (7 and 8) in the barrels (5 and 6). The shapes of the integrally operating means (4) can be various, and the shape shown in FIG. 3 is one of them. Two grooves parallel to each other and keeping plates vertical to the grooves are integrally molded for fixing the pressing parts of the plungers (7 and 8). The shape of the grooves is almost similar to that of the grooves of the syringe-holding means (3) so that each pressing part is fixed in the groove and thereby kept therein. A gap is provided between the groove and the keeping plate, which varies depending on the pressing part of the plunger (7 or 8). The syringe-holding means (3) and the integrally operating means (4) are usually made from a synthetic resin which is preferably polyethylene, polypropylene, acrylonitrile/butadiene/styrene copolymer or a polycarbonate.

The spray coating adhesive for tissue of the present invention is practically used as follows: The syringe (1) filled with the fibrinogen solution and the syringe (2) filled with the thrombin solution are fixed in the syringe-holding means (3). The volume ratio of the fibrinogen solution to the thrombin solution in the syringes (1 and 2) varies depending on the cross section of each syringe. A pair of the syringes (1 and 2) are mounted in the spray head (9). The pressure of the sterile gas to be jetted is controlled, and the gas is then jetted. Then, the integrally operating means (4) is slowly pressed with the thumb to simultaneously apply the fibrinogen solution and the thrombin solution in a mist form, by means of the sterile gas.

Industrial Utilization

The tissue adhesive of the present invention is useful for the adhesion or closing of living tissue of a human being or an animal, when a strong adhesion and closing effect are demanded in, for example, the treatment of great vessels and also the treatment of air leak in the lungs.

What is claimed is:

1. An adhesive for tissue comprising a fibrinogen solution and a thrombin solution which solutions are separated from each other, said adhesive being to be mixed and sprayed together with a sterile gas for the adhesion or closing of living tissue of a human being or animal, wherein the volume ratio of the fibrinogen solution to the thrombin solution is at least about 5:1.

2. The adhesive of claim 1, wherein the volume ratio of the fibrinogen solution to the thrombin solution is about 5:1 to 10:1.

3. The adhesive of claim 1, wherein the fibrinogen solution has a concentration of 4 to 15% (w/v, 40 to 150 mg/ml).

4. The adhesive of claim 3, wherein the fibrinogen solution has a concentration of 7 to 12% (w/v, 70 to 120 mg/ml).

5. The adhesive of claim 1, wherein the thrombin solution has a concentration of 100 to 10,000 units/ml (NIH units).

6. The adhesive of claim 5, wherein the thrombin solution has a concentration of 250 to 5,000 units/ml (NIH units).

7. The adhesive of claim 1, wherein the fibrinogen solution contains at least one viscosity-lowering agent.

8. The adhesive of claim 7, wherein the viscosity-lowering agent is arginine.

9. The adhesive of claim 8 which contains 0.1 to 1.0 M of arginine.

10. The adhesive of claim 9 which contains 0.1 to 0.5 M of arginine.

* * * * *

UNITED STATES PATENT AND TRADEMARK OFFICE
CERTIFICATE OF CORRECTION

PATENT NO. : 5,980,866
DATED : November 9, 1999
INVENTOR(S) : Takanori UCHIDA et al.

It is certified that error appears in the above-identified patent and that said Letters Patent is hereby corrected as shown below:

On the title page, item [73], the Assignee is incorrectly listed. It should be:

--[73] Assignee: Juridical Foundation The Chemo-Sero-Therapeutic Research Institute, Kumamoto, Japan--

Signed and Sealed this

Nineteenth Day of December, 2000

Attest:

Q. TODD DICKINSON

*Attesting Officer*

*Commissioner of Patents and Trademarks*